US009486578B2

(12) United States Patent
Finan et al.

(10) Patent No.: US 9,486,578 B2
(45) Date of Patent: Nov. 8, 2016

(54) METHOD AND SYSTEM FOR TUNING A CLOSED-LOOP CONTROLLER FOR AN ARTIFICIAL PANCREAS

(71) Applicant: Animas Corporation, West Chester, PA (US)

(72) Inventors: Daniel Finan, Philadelphia, PA (US); Thomas McCann, Pottstown, PA (US); Ramakrishna Venugopalan, Malvern, PA (US)

(73) Assignee: Animas Corporation, West Chester, PA (US)

( * ) Notice: Subject to any disclaimer, the term of this patent is extended or adjusted under 35 U.S.C. 154(b) by 757 days.

(21) Appl. No.: 13/708,032

(22) Filed: Dec. 7, 2012

(65) Prior Publication Data

US 2014/0163517 A1     Jun. 12, 2014

(51) Int. Cl.
| | |
|---|---|
| *G01N 33/48* | (2006.01) |
| *G01N 31/00* | (2006.01) |
| *G06G 7/48* | (2006.01) |
| *G06G 7/58* | (2006.01) |
| *A61M 5/172* | (2006.01) |
| *G06F 19/00* | (2011.01) |
| *A61M 5/142* | (2006.01) |

(52) U.S. Cl.
CPC ....... *A61M 5/1723* (2013.01); *A61M 5/14244* (2013.01); *G06F 19/345* (2013.01); *G06F 19/3456* (2013.01); *G06F 19/3468* (2013.01); *A61M 2005/14296* (2013.01); *A61M 2205/3553* (2013.01); *A61M 2205/3561* (2013.01); *A61M 2205/3592* (2013.01); *A61M 2205/702* (2013.01); *A61M 2209/01* (2013.01); *A61M 2230/005* (2013.01); *A61M 2230/201* (2013.01)

(58) Field of Classification Search
None
See application file for complete search history.

(56) References Cited

U.S. PATENT DOCUMENTS

| | | | |
|---|---|---|---|
| 4,055,175 A | 10/1977 | Clemens et al. | |
| 4,280,494 A | 7/1981 | Cosgrove, Jr. et al. | |
| 5,283,729 A | 2/1994 | Lloyd | |

(Continued)

FOREIGN PATENT DOCUMENTS

| | | | | |
|---|---|---|---|---|
| GB | 2466183 A | | 6/2010 | |
| WO | WO 2012/051344 | * | 4/2012 | ............. G06F 19/00 |

OTHER PUBLICATIONS

Ali, Emad, "Heuristic On-Line Tuning for Nonlinear Model Predictive Controllers Using Fuzzy Logic," J Process Control, 13(5), 383-396, 2003.

(Continued)

*Primary Examiner* — Larry D Riggs, II

(57) ABSTRACT

Described and illustrated is a system for management of diabetes that includes an infusion pump, glucose sensor and controller with a method programmed into the controller. The infusion pump is configured to deliver insulin to a subject. The glucose sensor is configured to sense glucose levels in the subject and provide output signals representative of the glucose levels in the subject. The controller is programmed receives signals from at least one of the glucose sensor and the pump and configured to issue signals to the pump to deliver an amount of insulin determined by a feedback controller that utilizes a model predictive control of the subject based on desired glucose levels, insulin amount delivered and measured glucose levels of the subject. The controller is also configured to deliver insulin using a tuning factor based on either one of an omission index module or a calibration index module.

7 Claims, 4 Drawing Sheets

(56) References Cited

U.S. PATENT DOCUMENTS

| | | | |
|---|---|---|---|
| 5,298,022 | A | 3/1994 | Bernardi |
| 5,347,446 | A | 9/1994 | Iino et al. |
| 7,060,059 | B2 | 6/2006 | Keith et al. |
| 7,276,029 | B2 | 10/2007 | Goode, Jr. et al. |
| 7,451,004 | B2 | 11/2008 | Thiele et al. |
| 7,577,483 | B2 | 8/2009 | Fan et al. |
| 8,046,089 | B2 | 10/2011 | Renfro et al. |
| 2002/0106709 | A1 | 8/2002 | Potts et al. |
| 2005/0192557 | A1 | 9/2005 | Brauker et al. |
| 2008/0287761 | A1 | 11/2008 | Hayter et al. |
| 2009/0156924 | A1 | 6/2009 | Shariati et al. |
| 2010/0057043 | A1 | 3/2010 | Kovatchev et al. |
| 2010/0179768 | A1 | 7/2010 | Kovatchev et al. |
| 2010/0305545 | A1 | 12/2010 | Kanderian, Jr. et al. |
| 2011/0196213 | A1 | 8/2011 | Thukral et al. |
| 2011/0208156 | A1 | 8/2011 | Doyle, III et al. |
| 2011/0257627 | A1 | 10/2011 | Hovorka |
| 2011/0264378 | A1 | 10/2011 | Breton et al. |
| 2011/0313680 | A1 | 12/2011 | Doyle, III et al. |
| 2012/0059353 | A1 | 3/2012 | Kovatchev et al. |
| 2012/0078067 | A1 | 3/2012 | Kovatchev et al. |
| 2012/0108932 | A1 | 5/2012 | Roy |
| 2012/0130698 | A1 | 5/2012 | Kovatchev et al. |
| 2012/0191361 | A1 | 7/2012 | Kovatchev et al. |
| 2012/0245556 | A1 | 9/2012 | Kovatchev et al. |
| 2012/0286953 | A1 | 11/2012 | Bousamra et al. |

OTHER PUBLICATIONS

Amrit, Rishi, "Model Predictive Control Tools Package," MPC Tools and Algorithm Details, Copyright (C) 2008 by University of Wisconsin, available at: http://jbrwww.che.wisc.edu/software/mpctools/method.html.

Amrit, Rishi et al., "Nonlinear Model Predictive Control Tools (NMPC Tools)," Apr. 5, 2008.

Amrit, Rishi, "Optimizing Process Economics in Model Predictive Control," Dissertation, University of Wisconsin-Madison, 2011, 193 pages.

Atlas, Eran et al., "MD-Logic Artificial Pancreas System," Diabetes Care, vol. 33, No. 5, May 2010.

Bequette, B. Wayne, "Analysis of Algorithms for Intensive Care Unit Blood Glucose Control," Journal of Diabetes Science and Technology, vol. 1, Issue 6, Nov. 2007, 813-824.

Breton, Marc et al., "Fully Integrated Artificial Pancreas in Type 1 Diabetes," from diabetes.diabetesjournals.org, Diabetes Publish Ahead of Print, published online Jun. 11, 2012, 8 pages.

Buckingham, Bruce, "Update on Closed-Loop Therapies," Presentation, Stanford Medical Center, 123 pages.

Clarke, William L. et al., "Closed-Loop Artificial Pancreas Using Subcutaneous Glucose Sensing and Insulin Delivery and a Model Predictive Control Algorithm: The Virginia Experience," Journal of Diabetes Science and Technology, vol. 3, Issue 5, Sep. 2009.

Cobelli, Claudio et al., "Artificial Pancreas: Past, Present, Future," Diabetes vol. 60, Nov. 2011.

Ellingsen, Christian et al., "Safety Constraints in an Artificial Pancreatic β Cell: An Implementation of Model Predictive Control with Insulin on Board," Journal of Diabetes Science and Technology, vol. 3, Issue 3, May 2009.

Fukushima, Hiroaki et al., "Robust Constrained Model Predictive Control using Closed-loop Prediction," Department of Systems Science, Kyoto University, 29 pages.

Gillis, Rachel et al., "Glucose Estimation and Prediction through Meal Responses Using Ambulatory Subject Data for Advisory Mode Model Predictive Control," Journal of Diabetes Science and Technology vol. 1, Issue 6, Nov. 2007.

Gonzalez, Alejandro H. et al., "A stable MPC with zone control," Science Direct, Journal of Process Control 19 (2009) 110-122.

Gonzalez, Alejandro H. et al., "Robust Model Predictive Control for Time Delayed Systems with Optimizing Targets and Zone Control," Robust Control, Theory and Applications, Prof. Andrzej Bartoszewicz (Ed.), ISBN: 978-953-307-229-6, InTech, 2011, Available from: http://www.intechopen.com/books/robust-control-theory-and-applications/robust-model-predictive-control-fortime-delayed-systems-with-optimizing-targets-and-zone-control.

Grosman, Benjamin et al., "Zone Model Predictive Control: A Strategy to Minimize Hyper and Hypoglycemic Events," Journal of Diabetes Science and Technology, vol. 4, Issue 4, Jul. 2010.

Haugan, Thomas, "Diploma Thesis: Real-Time Model Predictive Control," Automatic Control Laboratory, Swiss Federal Institute of Technology, Jun. 13, 2001, 117 pages.

Holkar, K. S. et al., "An Overview of Model Predictive Control," International Journal of Control and Automation, vol. 3, No. 4, Dec. 2010, 47-64.

Honeywell, "Closed Loop Identification for Model Predictive Control: Application to Air Separation Process," Advanced Solutions, Technical Information Note, 8 pages.

Hovd, Morten, "Improved Target Calculation for Model Predictive Control," Modeling, Identification and Control, vol. 28, No. 3, 2007, pp. 81-86.

Kerrigan, Eric C. et al., "Feedback min-max model predictive control using a single linear program: Robust stability and the explicit solution," Int. J. Robust Nonlinear Control 2004; 14:395-413.

Kovatchev, Boris et al., "Control to Range for Diabetes: Functionality and Modular Architecture," Journal of Science and Technology, vol. 3, Issue 5, Sep. 2009.

Kovatchev, Boris et al., "Multinational Study of Subcutaneous Model-Predictive Closed-Loop Control in Type 1 Diabetes Mellitus: Summary of the Results," Journal of Diabetes Science and Technology, vol. 4, Issue 6, Nov. 2010.

Lee et al., "A Closed-Loop Artificial Pancreas based on MPC: Human Friendly Identification and Automatic Meal Disturbance Rejection," Proceedings of the 17th World Congress, The International Federation of Automatic Control, Seoul Korea Jul. 6-11, 2008.

Lee et al., "A Closed-Loop Artificial Pancreas Using Model Predictive Control and a Sliding Meal Size Estimator," Journal of Diabetes Science and Technology, vol. 3, Issue 5, Sep. 2009.

Maciejowski, J.M., "Predictive Control With Constraints," Harlow, UK: Prentice-Hall, Pearson Education Limited, 2002.

Magni et al., "Model Predictive Control of Type 1 Diabetes: An in Silico Trial," Journal of Diabetes Science and Technology, vol. 1, Issue 6, Nov. 2007.

Magni et al., "Run-to-Run Tuning of Model Predictive Control for Type 1 Diabetes Subjects: In Silico Trial," Journal of Diabetes Science and Technology, vol. 3, Issue 5, Sep. 2009.

Mayne, D. Q. et al., "Constrained model predictive control: Stability and optimality," Automatica 36 (2000) 789-814.

MPC Controller, from Computer MPC control law—Simulink, available at: http://www.mathworks.com/help/mpc/ref/mpc-controller.html, Nov. 19, 2012.

MPC—Controls Wiki, available at: http://controls.engin.umich.edu/wiki/index.php/MPC, Nov. 12, 2012.

Percival et al., "Closed-Loop Control of an Artificial Pancreatic β-Cell Using Multi-Parametric Model Predictive Control," Diabetes Research 2008.

Percival et al., "Closed-Loop Control and Advisory Mode Evaluation of an Artificial Pancreatic β Cell: Use of Proportional-Integral-Derivative Equivalent Model-Based Controllers," Journal of Diabetes Science and Technology, vol. 2, Issue 4, Jul. 2008.

Plank, Plank et al., "Multicentric, Randomized, Controlled Trial to Evaluate Blood Glucose Control by the Model Predictive Control Algorithm Versus Routine Glucose Management Protocols in Intensive Care Unit Patients," Diabetes Care, vol. 29, No. 2, Feb. 2006.

Schridhar, Schridhar et al., "A Tuning Strategy for Unconstrained Multivariable Model Predictive Control," Ind. Eng. Chem. Res. 1998, 37, 4003-4016.

Shead, L.R.E. et al., "Conditions for which linear MPC converges to the correct target," Journal Process Control 20 (2010) 1243-1251.

Soru, Paola et al.., "MPC Based Artificial Pancreas: Strategies for Individualization and Meal Compensation," Annual Reviews in Control 36, p. 118-128 (2012).

(56) References Cited

OTHER PUBLICATIONS

Tassa, Yuval et al., "Fast Model Predictive Control for Reactive Robotic Swimming," Publication date not known.

Tenny, Matthew J. et al., "Closed-loop Behavior of Nonlinear Model Predictive Control," Texas-Wisconsin Modeling and Control Consortium, Technical report No. 2002-04, 32 pages.

Wang et al., "Automatic Bolus and Adaptive Basal Algorithm for the Artificial Pancreatic β-Cell," Diabetes Technology and Therapeutics, vol. 12, No. 11, 2010.

Wang, Youqing et al., "Closed-Loop Control of Artificial Pancreatic β-Cell in Type 1 Diabetes Mellitus Using Model Predictive Iterative Learning Control," IEEE Transactions on Biomedical Engineering, vol. 57, No. 2, Feb. 2010.

Zermani, M. A. et al., "Self-tuning weighting factor to decoupling control for incubator system," IJITCA vol. 2, No. 3, Jul. 2012.

International Search Report issued in related International Patent Application No. PCT/US13/73289, Apr. 10, 2014, 4 pages.

Written Opinion issued in related International Patent Application No. PCT/US13/73289, Apr. 10, 2014, 5 pages.

International Preliminary Report on Patentability issued in related International Patent Application No. PCT/US2013/03289, dated Jun. 9, 2015, 6 pages.

Supplementary European Search Report issued in related European Patent Application No. 13860173.7, dated Apr. 1, 2016, 8 pages.

* cited by examiner

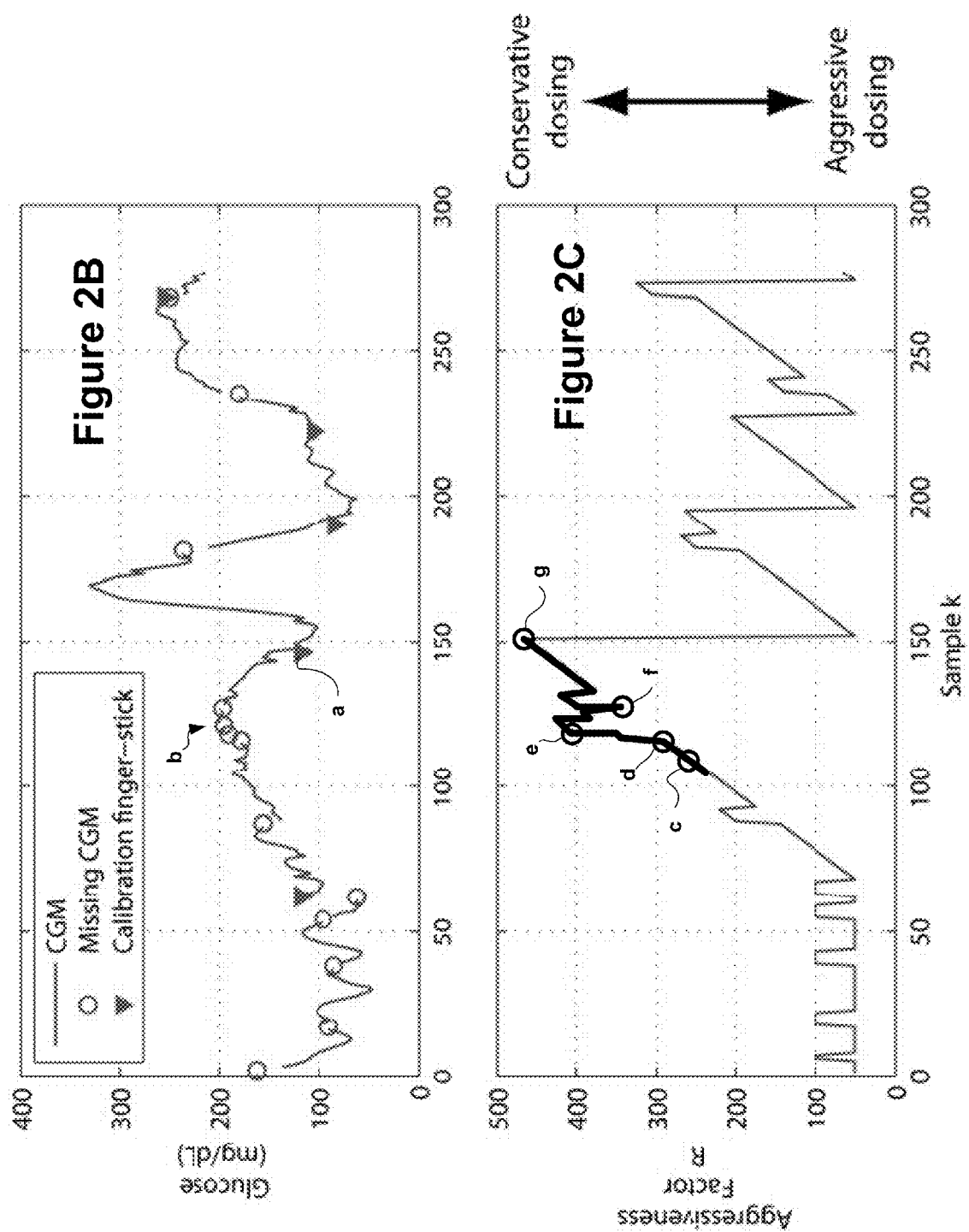

METHOD AND SYSTEM FOR TUNING A CLOSED-LOOP CONTROLLER FOR AN ARTIFICIAL PANCREAS

BACKGROUND

Diabetes mellitus is a chronic metabolic disorder caused by an inability of the pancreas to produce sufficient amounts of the hormone insulin, resulting in the decreased ability of the body to metabolize glucose. This failure leads to hyperglycemia, i.e. the presence of an excessive amount of glucose in the blood plasma. Persistent hyperglycemia and/or hypoinsulinemia has been associated with a variety of serious symptoms and life threatening long term complications such as dehydration, ketoacidosis, diabetic coma, cardiovascular diseases, chronic renal failure, retinal damage and nerve damages with the risk of amputation of extremities. Because restoration of endogenous insulin production is not yet possible, a permanent therapy is necessary which provides constant glycemic control in order to always maintain the level of blood glucose within normal limits. Such glycemic control is achieved by regularly supplying external insulin to the body of the patient to thereby reduce the elevated levels of blood glucose.

External biologic such as insulin was commonly administered by means of multiple daily injections of a mixture of rapid and intermediate acting drugs via a hypodermic syringe. It has been found that the degree of glycemic control achievable in this way is suboptimal because the delivery is unlike physiological hormone production, according to which hormone enters the bloodstream at a lower rate and over a more extended period of time. Improved glycemic control may be achieved by the so-called intensive hormone therapy which is based on multiple daily injections, including one or two injections per day of a long acting hormone for providing basal hormone and additional injections of rapidly acting hormone before each meal in an amount proportional to the size of the meal. Although traditional syringes have at least partly been replaced by insulin pens, the frequent injections are nevertheless very inconvenient for the patient, particularly those who are incapable of reliably self-administering injections.

Substantial improvements in diabetes therapy have been achieved by the development of the drug delivery device, relieving the patient of the need for syringes or drug pens and the administration of multiple daily injections. The drug delivery device allows for the delivery of drug in a manner that bears greater similarity to the naturally occurring physiological processes and can be controlled to follow standard or individually modified protocols to give the patient better glycemic control.

In addition, delivery directly into the intraperitoneal space or intravenously can be achieved by drug delivery devices. Drug delivery devices can be constructed as an implantable device for subcutaneous arrangement or can be constructed as an external device with an infusion set for subcutaneous infusion to the patient via the transcutaneous insertion of a catheter, cannula or a transdermal drug transport such as through a patch. External drug delivery devices are mounted on clothing, hidden beneath or inside clothing, or mounted on the body and are generally controlled via a user interface built-in to the device or on a separate remote device.

Blood or interstitial glucose monitoring is required to achieve acceptable glycemic control. For example, delivery of suitable amounts of insulin by the drug delivery device requires that the patient frequently determines his or her blood glucose level and manually input this value into a user interface for the external pumps, which then calculates a suitable modification to the default or currently in-use insulin delivery protocol, i.e., dosage and timing, and subsequently communicates with the drug delivery device to adjust its operation accordingly. The determination of blood glucose concentration is typically performed by means of an episodic measuring device such as a hand-held electronic meter which receives blood samples via enzyme-based test strips and calculates the blood glucose value based on the enzymatic reaction.

Continuous glucose monitoring (CGM) has also been utilized over the last twenty years with drug delivery devices to allow for closed loop control of the insulin(s) being infused into the diabetic patients. To allow for closed-loop control of the infused insulins, proportional-integral-derivative ("PID") controllers have been utilized with mathematical model of the metabolic interactions between glucose and insulin in a person. The PID controllers can be tuned based on simple rules of the metabolic models. However, when the PID controllers are tuned or configured to aggressively regulate the blood glucose levels of a subject, overshooting of the set level can occur, which is often followed by oscillations, which is highly undesirable in the context of regulation of blood glucose. Alternative controllers were investigated. It was determined that a model predictive controller ("MPC") used in the petrochemical industries where processes involved large time delays and system responses, was the most suitable for the complex interplay between insulin, glucagon, and blood glucose. The MPC controller has been demonstrated to be more robust than PID because MPC considers the near future effects of control changes and constraints in determining the output of the MPC whereas PID typically involves only past outputs in determining future changes. Constraints can be implemented in the MPC controller such that MPC prevents the system from running away when the limit has already been reached. Another benefit of MPC controllers is that the model in the MPC can, in some cases, theoretically compensate for dynamic system changes whereas a feedback control, such as PID control, such dynamic compensation would not be possible.

MPC can be viewed therefore as a combination of feedback and feed forward control. MPC, however, typically requires a metabolic model to mimic as closely as possible the interaction between insulin and glucose in a biological system. As such, due to person-to-person biological variations, MPC models continue to be further refined and developed and details of the MPC controllers, variations on the MPC and mathematical models representing the complex interaction of glucose and insulin are shown and described in the following documents:

U.S. Pat. No. 7,060,059;

US Patent Application Nos. 2011/0313680 and 2011/0257627,

International Publication WO 2012/051344,

Percival et al., *"Closed-Loop Control and Advisory Mode Evaluation of an Artificial Pancreatic β Cell: Use of Proportional-Integral-Derivative Equivalent Model-Based Controllers"* Journal of Diabetes Science and Technology, Vol. 2, Issue 4, July 2008.

Paola Soru et al., *"MPC Based Artificial Pancreas; Strategies for Individualization and Meal Compensation"* Annual Reviews in Control 36, p. 118-128 (2012), Cobelli et al., *"Artificial Pancreas: Past, Present, Future"* Diabetes Vol. 60, November 2011;

Magni et al., "*Run-to-Run Tuning of Model Predictive Control for Type 1 Diabetes Subjects: In Silico Trial*" Journal of Diabetes Science and Technology, Vol. 3, Issue 5, September 2009.

Lee et al., "*A Closed-Loop Artificial Pancreas Using Model Predictive Control and a Sliding Meal Size Estimator*" Journal of Diabetes Science and Technology, Vol. 3, Issue 5, September 2009;

Lee et al., "*A Closed-Loop Artificial Pancreas based on MPC: Human Friendly Identification and Automatic Meal Disturbance Rejection*" Proceedings of the 17$^{th}$ World Congress, The International Federation of Automatic Control, Seoul Korea Jul. 6-11, 2008;

Magni et al., "*Model Predictive Control of Type 1 Diabetes: An in Silico Trial*" Journal of Diabetes Science and Technology, Vol. 1, Issue 6, November 2007;

Wang et al., "*Automatic Bolus and Adaptive Basal Algorithm for the Artificial Pancreatic β-Cell*" Diabetes Technology and Therapeutics, Vol. 12, No. 11, 2010; and Percival et al., "*Closed-Loop Control of an Artificial Pancreatic β-Cell Using Multi-Parametric Model Predictive Control*" Diabetes Research 2008.

All articles or documents cited in this application are hereby incorporated by reference into this application as if fully set forth herein.

SUMMARY OF THE DISCLOSURE

Applicants have discovered a technique that allows for the tuning of the model predictive control based on two variables relating to calibration data and missing or incomplete CGM data. In particular, a method is provided to control an infusion pump with a controller to control the pump and receive data from at least one glucose sensor. The method can be achieved by: measuring glucose level in the subject from the glucose sensor to provide at least one glucose measurement in each time interval in a series of discrete time interval index ("k"); obtaining a glucose calibration measurement during at least one time interval in the series of time interval index to provide for a calibration index; ascertaining whether one or more glucose measurements were not provided during a time interval of the series of time interval index to provide for an omission index; determining a tuning factor based on both the calibration index and omission index; calculating insulin amount for delivery by the controller based on a model predictive controller that utilizes: (a) the plurality of glucose measurements to predict a trend of the glucose level from estimates of a metabolic state of the subject and (b) the tuning factor so as to provide a calculated insulin amount to be delivered to the subject for each interval of the interval index; delivering an insulin amount determined from the calculating step.

In yet another aspect, a system for management of diabetes is provided that includes an episodic glucose meter, continuous glucose meter, and an infusion pump coupled to a controller. The episodic glucose meter is configured to measure blood glucose of a subject at discrete non-uniform time intervals and provide such episodic blood glucose levels as a calibration index for each interval in a time interval index (k). The continuous glucose monitor that continuously measures glucose level of the subject at discrete generally uniform time intervals and provide the glucose level at each interval in the form of glucose measurement data, in which any omission of a glucose measurement in any interval is stored in an omission index. The insulin infusion pump is controlled by the controller to deliver insulin to the subject. The controller is in communication with the pump, glucose meter and the glucose monitor in which the controller determines a tuning factor based on: (a) a calibration index derived from episodic blood glucose measurement and (b) an omission index for a model-predictive-control such that controller determines an insulin delivery rate for each time interval in the time interval index (k) from the model predictive control based on: (1) desired glucose concentration, (2) glucose concentration measured by the monitor at each interval of the interval index (k), and (3) the tuning factor.

In each of the above aspects, the following features may also be utilized in combination with each of the aspects. For example, the at least one glucose sensor may include both a continuous glucose sensor and an episodic glucose meter; and the tuning factor may be derived from an equation of the form $$R(k) = R_{NOM} + r_1 * \text{CAL}(k) + r_2 * \text{MISSED}(k)$$

where:
- (k) may be a tuning factor at each time interval index k such that $R_{MIN} \leq R(k) \leq R_{MAX}$;
- $R_{NOM}$ may be a predetermined nominal tuning factor;
- k may be a discrete time interval index;
- $R_{NOM} \leq R_{MAX} \leq 100 * R_{NOM}$;
- $R_{NOM}/100 \leq R_{MIN} \leq R_{NOM}$;
- $(R_{MAX} - R_{MIN})/500 \leq r_1 \leq (R_{MAX} - R_{MIN})/50$;
- $(R_{MAX} - R_{MIN})/50 \leq r_2 \leq (R_{MAX} - R_{MIN})/5$;
- CAL(k) may be a calibration index in which
- CAL(k) = k - $k_{cal}$ - 6 (for k - $k_{cal} \geq 6$) or
- CAL(k) = k - $k_{cal2}$ - 6 (for k - $k_{cal} < 6$);
- $k_{cal}$ may be the sample index of the most recent calibration for the continuous glucose sensor;
- $k_{cal2}$ may be the sample index of the second most recent calibration for the continuous glucose sensor;
- MISSED(k) may be an omission index in which one or more glucose values during the series of time intervals of the index k are missing or unreported to the controller.

In each of the above aspects, the value for $r_1$ can be any number from about 1 to about 50 and for $r_2$ can be any number from about 10 to about 500.

These and other embodiments, features and advantages will become apparent to those skilled in the art when taken with reference to the following more detailed description of various exemplary embodiments of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

FIG. 2B illustrates a plot of glucose value for index k=0 to 300 in which other events such as missing CGM data or calibration measurements are superimposed on the glucose value plot.

FIG. 2C illustrates the tuning factor on the same scale of the index k=0 to 300 in which the tuning factor R is varied due to missing CGM data and calibration measurement.

MODES FOR CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. In addition, as used herein, the terms "patient," "host," "user," and "subject" refer to any human or animal subject and are not intended to limit the systems or methods to human use, although use of the subject invention in a human patient represents a preferred embodiment. Furthermore, the term "user" includes not only the patient using a drug infusion device but also the caretakers (e.g., parent or guardian, nursing staff or home care employee). The term "drug" may include hormone, biologically active materials, pharmaceuticals or other chemicals that cause a biological response (e.g., glycemic response) in the body of a user or patient.

Figure 1:
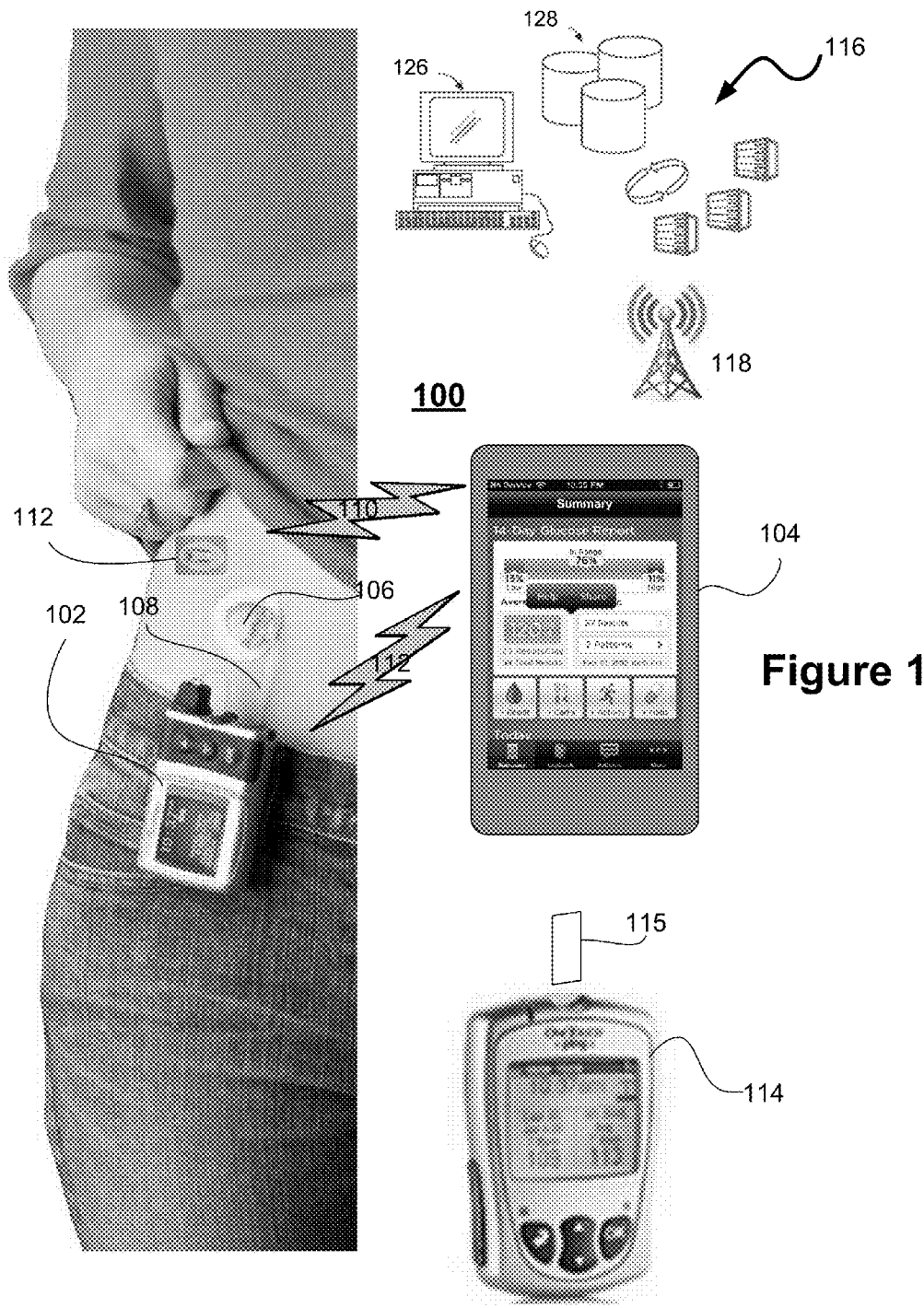
FIG. 1 illustrates the system in which a controller for the pump or glucose monitor(s) is separate from both the infusion pump and the glucose monitor(s) and in which a network can be coupled to the controller to provide near real-time monitoring.

FIG. 1 illustrates a drug delivery system 100 according to an exemplary embodiment that utilizes the principles of the invention. Drug delivery system 100 includes a drug delivery device 102 and a remote controller 104. Drug delivery device 102 is connected to an infusion set 106 via flexible tubing 108.

Drug delivery device 102 is configured to transmit and receive data to and from remote controller 104 by, for example, radio frequency communication 112. Drug delivery device 102 may also function as a stand-alone device with its own built in controller. In one embodiment, drug delivery device 102 is an insulin infusion device and remote controller 104 is a hand-held portable controller. In such an embodiment, data transmitted from drug delivery device 102 to remote controller 104 may include information such as, for example, insulin delivery data, blood glucose information, basal, bolus, insulin to carbohydrates ratio or insulin sensitivity factor, to name a few. The controller 104 is configured to include an MPC controller 10 that has been programmed to receive continuous glucose readings from a CGM sensor 112. Data transmitted from remote controller 104 to insulin delivery device 102 may include glucose test results and a food database to allow the drug delivery device 102 to calculate the amount of insulin to be delivered by drug delivery device 102. Alternatively, the remote controller 104 may perform basal dosing or bolus calculation and send the results of such calculations to the drug delivery device. In an alternative embodiment, an episodic blood glucose meter 114 may be used alone or in conjunction with the CGM sensor 112 to provide data to either or both of the controller 104 and drug delivery device 102. Alternatively, the remote controller 104 may be combined with the meter 114 into either (a) an integrated monolithic device; or (b) two separable devices that are dockable with each other to form an integrated device. Each of the devices 102, 104, and 114 has a suitable micro-controller (not shown for brevity) programmed to carry out various functionalities.

Drug delivery device 102 may also be configured for bi-directional wireless communication with a remote health monitoring station 116 through, for example, a wireless communication network 118. Remote controller 104 and remote monitoring station 116 may be configured for bi-directional wired communication through, for example, a telephone land based communication network. Remote monitoring station 116 may be used, for example, to download upgraded software to drug delivery device 102 and to process information from drug delivery device 102. Examples of remote monitoring station 116 may include, but are not limited to, a personal or networked computer 126, server 128 to a memory storage, a personal digital assistant, other mobile telephone, a hospital base monitoring station or a dedicated remote clinical monitoring station.

Drug delivery device 102 includes electronic signal processing components including a central processing unit and memory elements for storing control programs and operation data, a radio frequency module 116 for sending and receiving communication signals (i.e., messages) to/from remote controller 104, a display for providing operational information to the user, a plurality of navigational buttons for the user to input information, a battery for providing power to the system, an alarm (e.g., visual, auditory or tactile) for providing feedback to the user, a vibrator for providing feedback to the user, a drug delivery mechanism (e.g. a drug pump and drive mechanism) for forcing a insulin from a insulin reservoir (e.g., a insulin cartridge) through a side port connected to an infusion set 108/106 and into the body of the user.

Glucose levels or concentrations can be determined by the use of the CGM sensor 112. The CGM sensor 112 utilizes amperometric electrochemical sensor technology to measure glucose with three electrodes operably connected to the sensor electronics and are covered by a sensing membrane and a biointerface membrane, which are attached by a clip.

The top ends of the electrodes are in contact with an electrolyte phase (not shown), which is a free-flowing fluid phase disposed between the sensing membrane and the electrodes. The sensing membrane may include an enzyme, e.g., glucose oxidase, which covers the electrolyte phase. In this exemplary sensor, the counter electrode is provided to balance the current generated by the species being measured at the working electrode. In the case of a glucose oxidase based glucose sensor, the species being measured at the working electrode is $H_2O_2$. The current that is produced at the working electrode (and flows through the circuitry to the counter electrode) is proportional to the diffusional flux of $H_2O_2$. Accordingly, a raw signal may be produced that is representative of the concentration of glucose in the user's body, and therefore may be utilized to estimate a meaningful glucose value. Details of the sensor and associated components are shown and described in U.S. Pat. No. 7,276,029, which is incorporated by reference herein as if fully set forth herein this application. In one embodiment, a continuous glucose sensor from the Dexcom Seven System® (manufactured by Dexcom Inc.) can also be utilized with the exemplary embodiments described herein.

In one embodiment of the invention, the following components can be utilized as a system for management of diabetes that is akin to an artificial pancreas: OneTouch Ping® Glucose Management System by Animas Corporation that includes at least an infusion pump and an episodic glucose sensor; and DexCom® SEVEN PLUS® CGM by DexCom Corporation with interface to connect these components and programmed in MATLAB® language and accessory hardware to connect the components together; and control algorithms in the form of an MPC that automatically regulates the rate of insulin delivery based on the glucose level of the patient, historical glucose measurement and anticipated future glucose trends, and patient specific information.

Figure 2A:
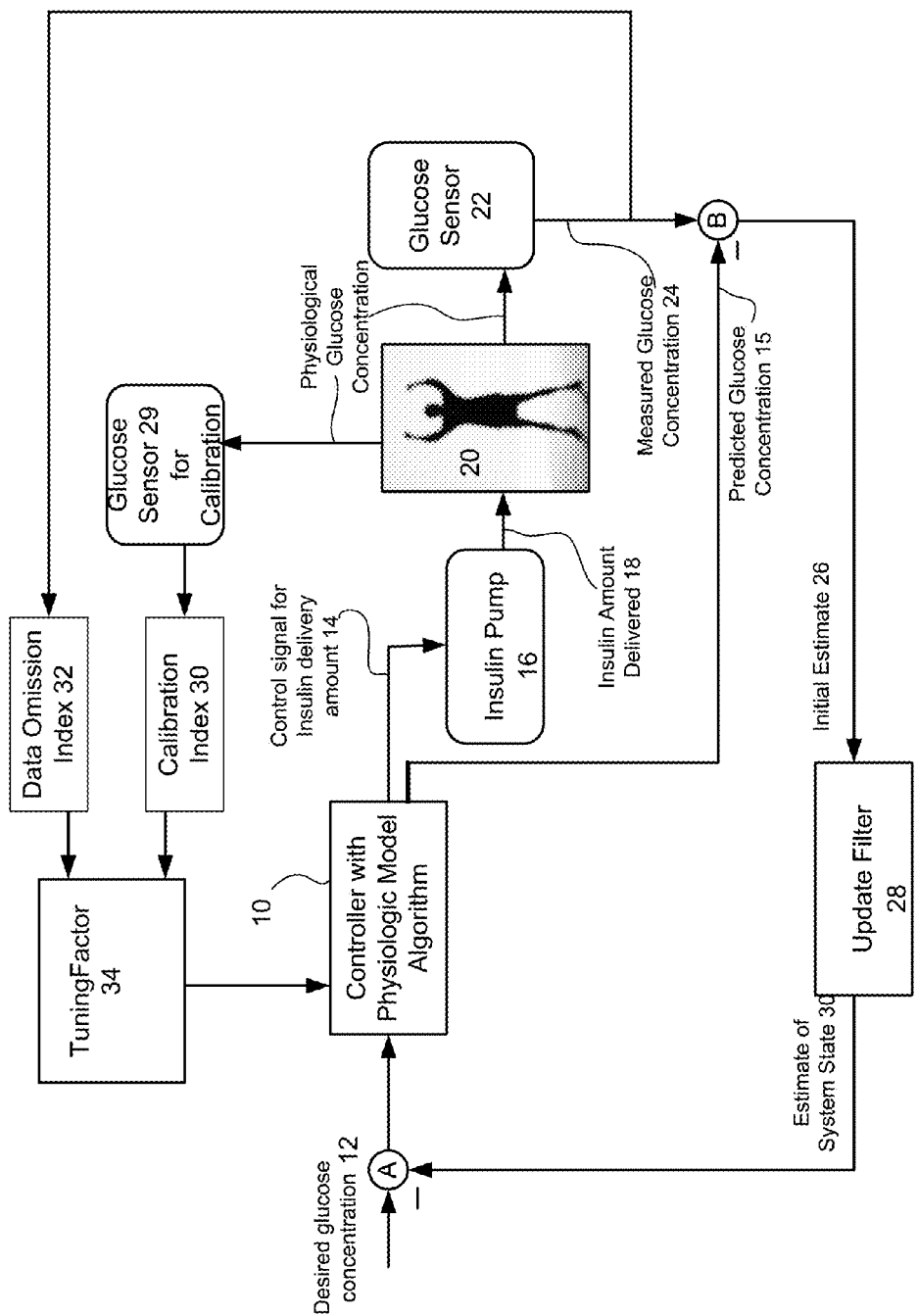
FIG. 2A illustrates an exemplary embodiment of the diabetic management system in schematic form.

FIG. 2A illustrates a schematic diagram 200 of the system 100 in FIG. 1 programmed with the solution devised by applicants to counteract a less than desirable effect of a closed-loop control system. In particular, FIG. 2A provides for an MPC programmed into a control logic module 10 that is utilized in controller 104. MPC logic module 10 receives a desired glucose concentration or range of glucose concentration 12 (along with any modification from an update filter 28 so that it is able to maintain the output (i.e., glucose level) of the subject within the desired range of glucose levels.

Referring to FIG. 2A, the first output 14 of the MPC-enabled control logic 10 can be a control signal to an insulin pump 16 to deliver a desired quantity of insulin 18 into a subject 20 at predetermined time intervals, which can be indexed every 5 minutes using time interval index k. A second output in the form of a predicted glucose value 15 can be utilized in control junction B. A glucose sensor 22 (or 112 in FIG. 1) measures the glucose levels in the subject 20 in order to provide signals 24 representative of the actual or measured glucose levels to control junction B, which takes the difference between measured glucose concentration 24 and the MPC predictions of that measured glucose concentration. This difference provides input for the update filter 26 of state variables of the model. The difference 26 is provided to an estimator (also known as an update filter 28) that provides for estimate of state variables of the model that cannot be measured directly. The update filter 28 is preferably a recursive filter in the form of a Kalman filter with tuning parameters for the model. The output of the update or recursive filter 28 is provided to control junction A whose output is utilized by the MPC in the control logic 10 to further refine the control signal 14 to the pump 16 (or 102 in FIG. 1). A tuning factor 34 is used with the MPC controller 10 to "tune" the controller in its delivery of the insulin. To accomplish this, applicants have devised the use of a calibration index module 30 and data omission module 32 to adjust the tuning factor. Calibration index module 30 is configured to track the number of glucose measurement calibration, which is typically accomplished by an episodic glucose monitor, such as, for example, a blood glucose test strip and meter system. Data omission index module 32 is configured to track the number of missing measurements or data from the continuous glucose monitor 22.

A brief overview of the MPC noted above that is used in control logic 10 is warranted here. The MPC logic is formulated to control a subject glucose level to a safe glucose zone, with the lower blood glucose limit of the zone varying between 80-100 mg/dL and the upper blood glucose limit varying between about 140-180 mg/dL; the algorithm will henceforth be referred to as the "zone MPC". Controlling to a target zone is, in general, applied to controlled systems that lack a specific set point with the controller's goal being to keep the controlled variable, (CV), for example the glucose values, in a predefined zone. Control to zone (i.e., a normaglycemic zone) is highly suitable for the artificial pancreas because of the absence of a natural glycemic set point. Moreover, an inherent benefit of control to zone is the ability to limit pump actuation/activity in a way that if glucose levels are within the zone then no extra correction shall be suggested.

In real-time, the insulin delivery rate $I_D$ from the zone MPC law is calculated by an on-line optimization, which evaluates at each sampling time the next insulin delivery rate. The optimization at each sampling time is based on the estimated metabolic state (plasma glucose, subcutaneous insulin) obtained from the dynamic model stored in module 10.

The MPC of control logic 10 incorporates an explicit model of human T1DM glucose-insulin dynamics. The model is used to predict future glucose values and to calculate future controller moves that will bring the glucose profile to the desired range. MPC in controllers can be formulated for both discrete- and continuous-time systems; the controller is set in discrete time, with the discrete time (stage) index k referring to the epoch of the $k^{th}$ sample occurring at continuous time $t = k \cdot T_s$, where $T_s = 5$ min is the sampling period. Software constraints ensure that insulin delivery rates are constrained between minimum (i.e., zero) and maximum values. The first insulin infusion (out of N steps) is then implemented. At the next time step, k+1 based on the new measured glucose value and the last insulin rate, the process is repeated.

Specifically, we start with the original linear difference model used for zone MPC:

$$G'(k) = a_1 G'(k-1) + a_2 G'(k-2) + a_3 G'(k-3) + a_4 G'(k-4) + a_5 G'(k-5) + b I_M(k-4) I_M(k) = c_1 I_M(k-1) + c_2 I_M(k-2) + d_1 I'_D(k-1) + d_2 I'_D(k-2) \quad \text{Eq. (1)}$$

where:
k is the discrete time interval index having a series of indexing counters where k=1, 2, 3 . . . .
G' is the measured glucose concentration
$I_M$ is the "mapped insulin" which is not a measured quantity
$I'_D$ is the delivered insulin or a manipulated variable
and coefficients $a_1 \sim 2.993$; $a_2 \sim (-3.775)$; $a_3 \sim 2.568$; $a_4 \sim (-0.886)$; $a_5 \sim 0.09776$; $b \sim (-1.5)$; $c_1 \sim 1.665$; $c_2 \sim (-0.693)$; $d_1 \sim 0.01476$; $d_2 \sim 0.01306$.

Using the FDA accepted metabolic simulator known to those skilled in the art, Eq. (1) can be reduced to the following linear difference model in Equation (2):

$$\text{(a)} \quad G'(k) = 2.993 G'(k-1) - 3.775 G'(k-2) + 2.568 G'(k-3) - 0.886 G'(k-4) + 0.09776 G'(k-5) - 1.5 I_M(k-4) + 0.1401 Meal_M(k-2) + 1.933 Meal_M(k-3)$$

$$\text{(b)} \quad I_M(k) = 1.665 I_M(k-1) - 0.693 I_M(k-2) + 0.01476 I'_D(k-1) + 0.01306 I'_D(k-2)$$

$$\text{(c)} \quad Meal_M(k) = 1.501 Meal_M(k-1) + 0.5427 Meal_M(k-2) + 0.02279 Meal(k-1) + 0.01859 Meal(k-2)$$

where:
G' is the glucose concentration output (G) deviation variable (mg/dL), i.e., $G' \equiv G - 110$ mg/dL,
$I_D'$ is the insulin infusion rate input ($I_D$) deviation variable (U/h), i.e., $I_D' \equiv I_D - \text{basal U/h}$, Meal is the CHO ingestion input (gram-CHO),
$I_M$ is the mapped subcutaneous insulin infusion rates (U/h), and
$Meal_M$ is the mapped CHO ingestion input (gram-CHO).

The dynamic model in Eq. (2) relates the effects of insulin infusion rate ($I_D$), and CHO ingestion input (Meal) on plasma glucose. The model represents a single average model for the total population of subjects. The model and its parameters are fixed.

The second-order input transfer functions described by parts (b) and (c) in Eq. (2) are used to generate an artificial input memory in the zone MPC schema to prevent insulin over-dosing, and consequently prevent hypoglycemia. In order to avoid over-delivery of insulin, the evaluation of any sequential insulin delivery must take into consideration the past administered insulin against the length of the insulin action. However, a one-state linear difference model with a relatively low order uses the output (glycemia) as the main source of past administered input (insulin) "memory." In the face of the model mismatch, noise, or change in the subject's insulin sensitivity, this may result in under- or over-delivery of insulin. This is mitigated by adding two additional states ($I_M$ and $Meal_M$) for the mapped insulin and meal inputs that carry a longer insulin memory.

Zone MPC is applied when the specific set point value of a controlled variable (CV) is of low relevance compared to a zone that is defined by upper and lower boundaries. Moreover, in the presence of noise and model mismatch there is no practical value using a fixed set point. Zone MPC was developed through research by the University of California at Santa Barbara and the Sansum Diabetes Research Institute. Other details of the derivation for the Zone MPC technique are shown and described in Benyamin Grosman, Ph.D., Eyal Dassau, Ph.D., Howard C. Zisser, M.D., Lois Jovanovič, M.D., and Francis J. Doyle III, Ph.D. *"Zone Model Predictive Control: A Strategy to Minimize Hyper and Hypoglycemic Events"* Journal of Diabetes Science and Technology, Vol. 4, Issue 4, July 2010, and US Patent Application Publication No. 2011/0208156 to Doyle et al., entitled "Systems, Devices, and Methods to Deliver Biological Factors or Drugs to a Subject," with the publication date of Aug. 25, 2011, all which are incorporated by reference as if set forth herein with a copy in the Appendix. Additional details of the Zone MPC are shown and described in US Patent Application Publication No. 20110208156, which is incorporated by reference as if set forth herein with a copy in the Appendix. A related derivation of zone MPC was presented in Maciejowski J M., *"PREDICTIVE CONTROL WITH CONSTRAINTS"* Harlow, UK: Prentice-Hall, Pearson Education Limited, 2002. The zone MPC is implemented by defining fixed upper and lower bounds as soft constraints by letting the optimization weights switch between zero and some final values when the predicted CVs are in or out of the desired zone, respectively. The predicted residuals are generally defined as the difference between the CV that is out of the desired zone and the nearest bound. Zone MPC is typically divided into three different zones. The permitted range is the control target and it is defined by upper and lower bounds. The upper zone represents undesirable high predicted glycemic values. The lower zone represents undesirable low predicted glycemic values that represent hypoglycemic zone or a pre-hypoglycemic protective area that is a low alarm zone. The zone MPC optimizes the predicted glycemia by manipulating the near-future insulin control moves to stay in the permitted zone under specified constrains.

The core of zone MPC lies in its cost function formulation that holds the zone formulation. Zone MPC, like any other forms of MPC, predicts the future output by an explicit model using past input/output records and future input moves that need to be optimized. However, instead of driving to a specific fixed set point, the optimization attempts to keep or move the predicted outputs into a zone that is defined by upper and lower bounds. Using a linear difference model, the glycemic dynamics are predicted and the optimization reduces future glycemic excursions from the zone under constraints and weights defined in its cost function.

The zone MPC cost function J used in the presented work is defined as follows:

$$J(I'_D) = Q \cdot \sum_{j=1}^{P} \|G^{zone}(k+j)\| + R \cdot \sum_{j=0}^{M-1} \|I'_D(k+j)\| \qquad (3)$$

s.t.

$$G(k+j) = f[G(k+j-1), I'_D(k+j-1)] \forall j = 1, P$$

$$-\text{basal}(k+j) \le I'_D(k+j) \le 72 \forall j = 0, M-1$$

or for our applications:

$$J(I_D') = \Sigma \|G^{zone}(k+j)\| + R \cdot \Sigma \|I_D(k+j) - \text{basal}(k+j)\| \qquad (4)$$

where
Q is a weighting factor on the predicted glucose term;
R is a tuning factor on the future proposed inputs in the cost function;
$f$ is the prediction function (in Eq. (2));
vector $I_D$ contains the set of proposed near-future insulin infusion amounts. It is the "manipulated variable" because it is manipulated in order to find the minimum in J.
$G^{zone}$ is a variable quantifying the deviation of future model-predicted CGM values G outside a specified glycemic zone, and is determined by making the following comparisons:

$$G^{zone} = \begin{cases} 0 & \text{if } G_{ZL} \le G \le G_{ZH} \\ G - G_{ZH} & \text{if } G > G_{ZH} \\ G_{ZL} - G & \text{if } G < G_{ZL} \end{cases} \qquad (5)$$

where the glycemic zone is defined by the upper limit $G_{ZH}$ and the lower limit $G_{ZL}$.

Thus, if all the predicted glucose values are within the zone, then every element of $G^{zone}$ is equal to 0, and consequently J is minimized with $I_D$=basal for that time of day, i.e., the algorithm "defaults" to the patient's current basal insulin infusion rate. On the other hand, if any of the predicted glucose values are outside the zone, then $G^{zone}>0$ and thus "contributes" to the cost function. In this case, the near-future proposed insulin infusion amounts $I_D$ will deviate from the basal in order to prevent out-of-zone deviation in $G^{zone}$ from ever happening, which will also "contribute" to the cost function. Then, a quantitative balance is found in the optimization, based on the weighting factor R.

In order to solve optimization problem of Equations (2)-(5), a commercially available software (e.g., MATLAB's "fmincon.m" function) is utilized. For this function, the following parameters are used for each optimization:
Initial guess for the insulin delivery rates, $I_D'(0)$, is the null vector $\vec{0} \in \mathbb{R}^M$, e.g., if M=5 the initial guess for each optimization is $I_D'=[0\ 0\ 0\ 0\ 0]$. This implies that the initial guess is equivalent to the basal rate.

Maximum number of function evaluations allowed is Max_f=100*M, where M is control horizon as described earlier.

Maximum number of iterations is Max_i=400, which is fixed.

Termination on the cost function values Term_cost=1e-6, which is fixed.

Termination tolerance Term_tol on the manipulated variables $I_D'$ is 1e-6.

The following hard constraints are implemented on the manipulated variables ($I_D'$):

$$-\text{basal} \leq I_D' \leq 74\ U/h \tag{6}$$

where basal is the subject's basal rate as set by the subject or his/her physician, expected in the range 0.6-1.8 U/hr.

Although the values of control horizontal parameter M and prediction horizon parameter P have significant effects on the controller performance, and are normally used to tune an MPC based controller, they can be heuristically tuned based on knowledge of the system. Tuning rules are known to those skilled in the field. According to these rules M and P may vary between:

$$2 \leq M \leq 10$$

$$20 \leq P \leq 120 \tag{7}$$

In the preferred embodiments, we use the nominal values of M=5 and P=108.

The ratio of the output error weighting factor Q and the input change weighting matrix or tuning factor R may vary between:

$$10 \leq \frac{R}{Q} \leq 1000 \tag{8}$$

In the preferred embodiments, we use the nominal value of R/Q=500.

Once the controller is initialized and switched on, realtime calculations take place every five minutes, corresponding to the sample time for the glucose sensor. The first element of $I_D$ is delivered as an insulin dose to the patient through the insulin pump, five minutes elapse, a new CGM reading becomes available, and the process repeats. It is noted that the future control moves are hard-constrained, set by the insulin pump's ability to deliver a maximum rate of insulin and the inability to deliver negative insulin values. Other details of related subject matter including state estimator, and other MPC are provided by Rachel Gillis et al., "*Glucose Estimation and Prediction through Meal Responses Using Ambulatory Subject Data for Advisory Mode Model Predictive Control*" Journal of Diabetes Science and Technology Vol. 1, Issue 6, November 2007 and by Youqing Wang et al., "*Closed-Loop Control of Artificial Pancreatic β-Cell in Type 1 Diabetes Mellitus Using Model Predictive Iterative Learning Control*" IEEE Transactions on Biomedical Engineering, Vol. 57, No. 2, February 2010, which are hereby incorporated by reference into this application as if fully set forth herein.

It is known that the tuning parameter (designated here as "R") can have a significant effect on the quality of the glucose control. The parameter—known as the aggressiveness factor, gain, and other names—determines the speed of response of the algorithm to changes in glucose concentration. A relatively conservative value of R results in a controller that is slow to adjust insulin infusion amounts (relative to basal) in response to changes in glucose; on the other hand, a relatively aggressive value of R results in a controller that is quick to respond to changes in glucose. In principle, an aggressive controller would result in the best glucose control if 1) the available glucose measurements are accurate, and moreover 2) the model predictions of future glucose trends are accurate. If these conditions are not true, then it may be safer to use a conservative controller.

A discussion of the tuning factor R (referenced here as 34) in FIG. 2A is worthwhile at this point. As it is not straightforward to determine either the accuracy of the glucose measurements on-line or the accuracy of the model predictions, it can be difficult to know the appropriate aggressiveness factor 34 or R to use for the current conditions. However, in specific circumstances, it is possible to ascertain with a high degree of certainty when a continuous glucose monitor (CGM) has become "less accurate" or "more accurate" in a qualitative sense.

Applicants believe that it is reasonable to assume that a CGM may become less accurate with each sample following a calibration, and has suddenly become less accurate when it fails to report a glucose measurement. Missed or omitted CGM measurements may be due to uncertainty in the glucose trend (a CGM algorithm feature) or simply to radio frequency communication issues. Similarly, it is reasonable to assume that the CGM has become more accurate following a calibration, and following a reestablishment of reporting glucose values after one or more missed readings.

Applicants have discovered therefore that it is possible to use these insights to tune the controller automatically, i.e., use a more conservative value of R for the aggressiveness factor when the CGM has become less accurate, and a more aggressive value when the CGM has become more accurate. This is demonstrated, in a general sense, below.

Let the aggressiveness factor, R, be bounded by the constants Rmin (for the most aggressive controller) and Rmax (for the most conservative controller):

$$R\text{min} <= R <= R\text{max} \tag{Eq. (9)}$$

Let there be two nominal increments, strictly positive quantities: $r_1$, a relatively small increment associated with the accuracy of a CGM in relation to how recent a calibration was, and $r_2$, a larger increment associated with the accuracy of a CGM as it pertains to missed samples.

The aggressiveness factor to be used in the MPC calculation for the current sampling instant, indexed by k, is R(k), where R(k) is automatically updated at each sample based on a nominal R value, $R_{NOM}$, which could in general be different for each user:

$$R(k)=R_{NOM}+r_1*\text{CAL}(k)+r_2*\text{MISSED}(k), \tag{Eq. (10)}$$

$$\text{and } R_{MIN} <= R(k) <= R_{MAX} \tag{Eq. (11)}$$

$$\text{CAL}(k)=k-k_{CAL}-6 \text{ for } k-k_{CAL}>=6 \tag{Eq.(12)}$$

$$\text{CAL}(k)=k-k_{CAL2}-6 \text{ for } k-k_{CAL}<6 \tag{Eq.(13)}$$

where:
$R_{NOM} \leq R_{MAX} \leq 100*R_{NOM}$
$R_{NOM}/100 \leq R_{MIN} \leq R_{NOM}$
$(R_{MAX}-R_{MIN})/500 \leq r_1 \leq (R_{MAX}-R_{MIN})/50$
$(R_{MAX}-R_{MIN})/50 \leq r_2 \leq (R_{MAX}-R_{MIN})/5$
CAL(k) is the calibration index.

It is noted that $R_{NOM}$ can be a value from about zero to about 1000 (e.g., $0 \leq R_{NOM} \leq 1000$; although it should be noted that this value and range are dependent on the specific cost function in the particular model being used and one skilled in the art would be able to configure the appropriate range for $R_{NOM}$, depending on the model being used. In the exemplary embodiments, $r_1$ can be any number from about 1 to about 50 and $r_2$ can be any number from about 10 to about 500.

The current sample index is k where $k_{CAL}$ is the sample index of the most recent CGM calibration with a suitable referential glucose analyzer or glucose meter 114, and $k_{CAL2}$ is the sample index of the second-most recent CGM calibration with a referential glucose meter 114. Thus, 30 min (e.g., 6 samples) following a calibration with the referential glucose meter 114, calibration index module 32 or CAL(k) is zero. Thereafter, CAL grows by one at each sample until the 30 min after the next calibration. This correction to the tuning factor R of module 34 at instance "k" (i.e., R(k)) results in a slightly more conservative controller (i.e., higher value of R for Equation (4)) with every consecutive CGM measurement by sensor 112 for each time interval index k, until the next calibration. The 30 minute buffer immediately following a calibration, during which the control logic 10 will act relatively conservatively, is due to potentially significant "jumps" in CGM values immediately following calibrations.

The omission index module 32 or MISSED(k) module determines the number (or index) of missed or omitted CGM samples from sensor 112 over the most recent five glucose sampling events. Thus, when the omission index module 32 or MISSED (k) returns a null or 0, this means that no CGM measurements from sensor 112 have been missed or omitted recently, and the control logic 10 is no more conservative. On the other hand, when 1<=MISSED(k)<=5, there has been at least one missed or omitted CGM measurement from sensor 112 recently, and the aggressiveness factor R or tuning factor 34 will increase by $r_2$*MISSED(k).

To demonstrate the operation of an embodiment of the invention, reference is made to FIGS. 2B and 2C along with Table 1. In this example, it is assumed that $R_{NOM}$ is about 50, $r_1$ is about 5, $r_2$ is about 50, $R_{MIN}$ is about 50 and $R_{MAX}$ is about 500. To further illustrate for this example how the omission index (referenced as "MISSED(k)") and calibration index (referenced as "CAL(k)") are used for determining the tuning factor R(k), Table 1 shows a portion (from index of k=110 to k=160) of the data plotted in FIGS. 2B and 2C.

TABLE 1

Exemplary calculations for the data plotted in FIGS. 2B and 2C based on the equation for R(k) and the parameter values $R_{NOM}$~50, $r_1$~5, $r_2$ ~, $R_{MIN}$~50 and $R_{MAX}$~500.

| Sample index k | CGM(k), mg/dL | MISSED(k) | Calibration finger-stick, mg/dL | CAL(k) | R(k) |
|---|---|---|---|---|---|
| 110 | 174 | 0 | | 42 | 260 |
| 111 | 173 | 0 | | 43 | 265 |
| 112 | 172 | 0 | | 44 | 270 |
| 113 | 171 | 0 | | 45 | 275 |
| 114 | 174 | 0 | | 46 | 280 |
| 115 | 178 | 0 | | 47 | 285 |
| 116 | — | 0 | | 48 | 290 |
| 117 | 190 | 1 | | 49 | 345 |
| 118 | — | 1 | | 50 | 350 |
| 119 | 196 | 2 | | 51 | 405 |
| 120 | 195 | 2 | | 52 | 410 |
| 121 | — | 2 | | 53 | 415 |
| 122 | 202 | 2 | | 54 | 420 |
| 123 | 199 | 2 | | 55 | 425 |
| 124 | 200 | 1 | | 56 | 380 |
| 125 | 197 | 1 | | 57 | 385 |
| 126 | 196 | 1 | | 58 | 390 |
| 127 | — | 0 | | 59 | 345 |
| 128 | 194 | 1 | | 60 | 400 |
| 129 | 194 | 1 | | 61 | 405 |
| 130 | 194 | 1 | | 62 | 410 |
| 131 | 182 | 1 | | 63 | 415 |
| 132 | 183 | 1 | | 64 | 420 |
| 133 | 190 | 0 | | 65 | 375 |
| 134 | 186 | 0 | | 66 | 380 |
| 135 | 183 | 0 | | 67 | 385 |
| 136 | 180 | 0 | | 68 | 390 |
| 137 | 176 | 0 | | 69 | 395 |
| 138 | 174 | 0 | | 70 | 400 |
| 139 | 172 | 0 | | 71 | 405 |
| 140 | 169 | 0 | | 72 | 410 |
| 141 | 166 | 0 | | 73 | 415 |
| 142 | 162 | 0 | | 74 | 420 |
| 143 | 143 | 0 | | 75 | 425 |
| 144 | 156 | 0 | | 76 | 430 |
| 145 | 152 | 0 | | 77 | 435 |
| 146 | 150 | 0 | 119 | 78 | 440 |
| 147 | 125 | 0 | | 79 | 445 |
| 148 | 124 | 0 | | 80 | 450 |
| 149 | 122 | 0 | | 81 | 455 |
| 150 | 120 | 0 | | 82 | 460 |
| 151 | 114 | 0 | | 83 | 465 |
| 152 | 108 | 0 | | 0 | 50 |
| 153 | 107 | 0 | | 1 | 55 |
| 154 | 106 | 0 | | 2 | 60 |
| 155 | 101 | 0 | | 3 | 65 |
| 156 | 109 | 0 | | 4 | 70 |
| 157 | 126 | 0 | | 5 | 75 |
| 158 | 116 | 0 | | 6 | 80 |
| 159 | 133 | 0 | | 7 | 85 |
| 160 | 157 | 0 | | 8 | 90 |

In FIG. 2B, it can be seen that there was one instance "a" of no calibration (▼) from time interval index 110 through 146 (from Table 1) and that there were multiple instances at "b" of missing CGM data (from time interval index 117-132 in Table 1). Based on the assumptions made by applicants regarding missing or omitted CGM data and the lack of calibration in the time interval index of k from 118 to 123, it is not surprising that the tuning factor R begins to rise at "c" with a slope starting at "d" that is nearly vertical until "e" before falling off at "f" and recovering towards "g" due to calibration ("a" in FIG. 2B) at index interval 146 (Table 1). Thus, it can be seen that from k~110 to k~160, the R factor is varied based on two indices (i.e., calibration "CAL" and omission "MISSED") to ensure that the blood glucose of the subject is within the upper limit of approximately 200 mg/dL (FIG. 2B)

To recap, the system of FIG. 2A is provided to manage diabetes of a subject. In this system, the following components are utilized: an episodic glucose meter 29, continuous glucose sensor 22, pump 16, and controller 10. The meter 29 measures blood glucose of a subject at discrete non-uniform time intervals (e.g., every 4 hours) and provide such episodic blood glucose level as a calibration index 30 for each interval in a time interval index (k where a time interval between k and k+1 is about 5 minutes). The continuous glucose monitor continuously measure glucose level of the subject at discrete generally uniform time intervals (e.g., approximately every 30 seconds or every minute) and provide the glucose level at each interval in the form of glucose measurement data, in which any omission of a glucose measurement in any interval is stored in an omission index 32. The insulin infusion pump is controlled by the controller 10 to deliver insulin to the subject 20. The controller 10 is programmed with the appropriate MPC program to control the pump and communicate with the glucose meter and the glucose monitor. In this aspect, the controller determines a tuning factor 34 based on (a) a calibration index 30 derived from episodic blood glucose measurements and (b) an omission index 32 for the MPC 10 such that controller determines an insulin delivery rate for each time interval in the time interval index (k) from the model predictive control based on (1) desired glucose concentration 12, (2) glucose concentration 24 measured by the monitor 22 at each interval of the interval index (k), and (3) the tuning factor 34.

Figure 3:
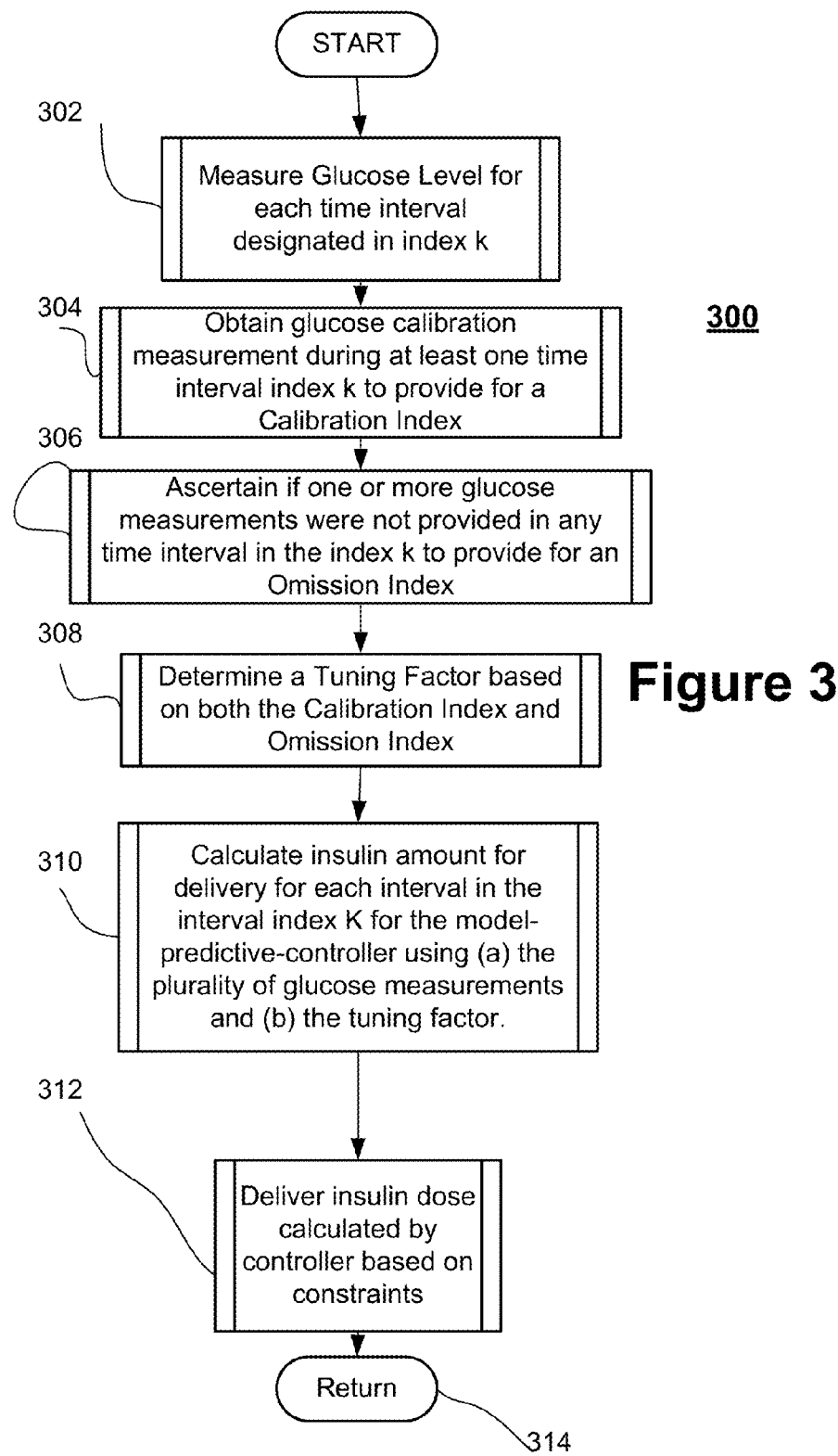
FIG. 3 illustrates the logic utilized in the controller of FIG. 1 or FIG. 2A.

By virtue of the disclosure provided herein, applicants have also devised a method to control an infusion pump to control an infusion pump with a controller to control the pump and receive data from at least one glucose sensor. With reference to FIG. 3, exemplary method will now be described. The method starts by measuring in step 302 a glucose level in the subject from the glucose sensor (22 or 29) to provide at least one glucose measurements in each time interval in a series of discrete time interval index ("k"). At step 304, the method obtains a glucose calibration measurement during at least one time interval in the series of time interval index k to provide for a calibration index that will be used in the tuning factor calculation of step 308. At step 306, the system ascertain whether one or more glucose measurements were not provided during a time interval of the series of time interval index k to provide for an omission index, which will also be used to determine the tuning factor R. At step 308, the method determines a tuning factor based on both the calibration index and omission index obtained previously. At step 310, the method calculates an insulin amount for delivery by the controller based on a model predictive controller that utilizes (a) the plurality of glucose measurements to predict a trend of the glucose level from estimates of a metabolic state of the subject and (b) the tuning factor so as to provide a calculated insulin amount to be delivered to the subject for each interval of the interval index. At step 312, the pump is controlled to deliver an insulin amount determined from the calculating step 310. At step 314, the routine returns to step 302 or another routine.

Clinical Scenarios.

In an in-silico study, the exemplary algorithm was investigated in the known FDA-approved simulation database of 100 adults under a pre-defined clinical protocol. The key features of the clinical protocol are:

Closed-loop control by the MPC for 26 hrs, beginning at a nominal 4 pm on Day 1 and ending at a nominal 6 pm on Day 2.

Three meals administered, at nominal times of 6 pm on Day 1 (a "dinner" meal), 7 am on Day 2 (a "breakfast" meal), and 12 pm on Day 2 (a "lunch" meal). Because the proposed clinical protocol includes flexibility regarding the carbohydrate (CHO) content of the meals, which can range from 30-70 g CHO, separate simulation scenarios were performed in which 30-g CHO meals were administered and 70-g CHO meals were administered.

Meal-related insulin boluses administered according the patient's insulin-to-CHO ratio, but they did not include a correction component.

The timing of the boluses relative to the meals has been designed to be adjustable between two paradigms, both of which were investigated in silico.

"Mealtime." In this paradigm, all meal-related boluses were administered at the start of the meals.

"Pre-meal." In this paradigm, meal-related boluses were administered 20 min prior to the start of the meal if the current CGM value was 100 mg/dL or higher. If the current CGM value was less than 100 mg/dL, the bolus was administered at the start of the meal.

In the event of a safety red alarm for hypoglycemia, the simulated subject was administered 16 g of CHO.

The first phase of clinical studies used a relatively conservative value of the tuning factor R=500. Building on these results, we investigated not only with this conservative value, but also two additional values: a medium value of R=250, and an aggressive value of R=50.

Taking these protocol and algorithm-related adjustable parameters into account, 12 unique simulation scenarios were crafted which investigate the spectrum of possible combinations proposed for the clinical study. These 12 scenarios are delineated in Table 2.

TABLE 2

Twelve simulation scenarios composing Stage 5 of the in-silico testing.

| Scenario | Aggressiveness Factor | Meal Bolus Timing | Meal Size |
| --- | --- | --- | --- |
| 8A | Conservative | Mealtime | 30 g CHO |
| 9A | Medium | Mealtime | 30 g CHO |
| 10A | Aggressive | Mealtime | 30 g CHO |
| 11A | Conservative | Pre-meal | 30 g CHO |
| 12A | Medium | Pre-meal | 30 g CHO |
| 13A | Aggressive | Pre-meal | 30 g CHO |
| 8B | Conservative | Mealtime | 70 g CHO |
| 9B | Medium | Mealtime | 70 g CHO |
| 10B | Aggressive | Mealtime | 70 g CHO |
| 11B | Conservative | Pre-meal | 70 g CHO |
| 12B | Medium | Pre-meal | 70 g CHO |
| 13B | Aggressive | Pre-meal | 70 g CHO |

Each of the scenarios in Table 2 was tested on the 100 adults in the FDA-accepted database, giving a grand total of 1,200 unique simulations for the Stage 5 studies.

Results.

Table 3 summarizes the results of each scenario in the Stage 5 simulations in terms of CGM values. Irrespective of the scenario, none of the patients experienced appreciable amounts of CGM values below 70 mg/dL. For the smaller, 30-g CHO meals, less than 1% of CGM values were above 180 mg/dL. The larger, 70-g CHO meals resulted in more time spent at CGM values above 180 mg/dL, but even in the "worst" case scenario—8B, using mealtime boluses and a conservative aggressiveness factor—only 5.5% of the closed-loop time was spent at these elevated glucose levels.

Table 3 also indicates that the effects of both the aggressiveness factor and the meal bolus timing on the resulting CGM levels were very subtle. For the 30-g CHO meals and either of the meal bolus timing paradigms, adjusting the aggressiveness factor from a conservative value to an aggressive value affected the frequency of CGM values within 70-180 mg/dL by only 0.1%. For the 70-g CHO meals, this value was just 0.7%.

The difference in CGM values between administering the meal-related boluses at mealtime versus 20 min prior to the meal was also subtle. For the 70-g CHO meals, for example, the pre-meal boluses resulted in 2.6% more time spent in the 70-180 mg/dL range relative to the mealtime boluses.

TABLE 3

Results for Stage 5 of the in-silico testing in terms of time spent in various glucose ranges (based on CGM values).

| Scenario | Aggressiveness Factor | Meal Bolus Timing | Time <70 mg/dL (%) | Time 70-180 mg/dL (%) | Time >180 mg/dL (%) |
|---|---|---|---|---|---|
| | | 30-g CHO meals | | | |
| 8A | Conservative | Mealtime | 0.0 | 99.8 | 0.2 |
| 9A | Medium | Mealtime | 0.0 | 99.7 | 0.3 |
| 10A | Aggressive | Mealtime | 0.0 | 99.7 | 0.2 |
| 11A | Conservative | Pre-meal | 0.0 | 100.0 | 0.0 |
| 12A | Medium | Pre-meal | 0.0 | 99.9 | 0.1 |
| 13A | Aggressive | Pre-meal | 0.0 | 100.0 | 0.0 |
| Average | | | 0.0 | 99.8 | 0.2 |
| | | 70-g CHO meals | | | |
| 8B | Conservative | Mealtime | 0.0 | 94.5 | 5.5 |
| 9B | Medium | Mealtime | 0.0 | 94.8 | 5.2 |
| 10B | Aggressive | Mealtime | 0.0 | 95.2 | 4.8 |
| 11B | Conservative | Pre-meal | 0.0 | 97.1 | 2.9 |
| 12B | Medium | Pre-meal | 0.0 | 97.2 | 2.8 |
| 13B | Aggressive | Pre-meal | 0.0 | 97.6 | 2.4 |
| Average | | | 0.0 | 96.1 | 3.9 |

The 12 scenarios in Table 3 tested the limits of the ranges of the adjustable algorithm parameter (the aggressiveness factor R of the zone MPC) and the adjustable protocol parameters (the meal size and the meal bolus timing).

Tables 4a and 4b present the data in Table 3 in arrays more conducive to assessing the effect of the aggressiveness factor or the bolus timing, while holding the other value constant.

TABLE 4a

Sensitivity of time spent at CGM values between 70-180 mg/dL (%) to the aggressiveness factor of the zone MPC (adjustable algorithm parameter) and the timing of the meal boluses (adjustable protocol parameter) - 30-g CHO meals.

| | | Aggressiveness Factor | | |
|---|---|---|---|---|
| Percentage of time spent 70-180 mg/dL | | Conservative (R = 500) | Medium (R = 250) | Aggressive (R = 50) |
| Meal Bolus Timing | Mealtime | 99.8% | 99.7% | 99.7% |
| | Pre-meal | 100.0% | 99.9% | 100.0% |

TABLE 4b

Sensitivity of time spent at CGM values between 70-180 mg/dL (%) to the aggressiveness factor of the zone MPC (adjustable algorithm parameter) and the timing of the meal boluses (adjustable protocol parameter) - 70-g CHO meals.

| | | Aggressiveness Factor | | |
|---|---|---|---|---|
| Percentage of time spent 70-180 mg/dL | | Conservative (R = 500) | Medium (R = 250) | Aggressive (R = 50) |
| Meal Bolus Timing | Mealtime | 94.5% | 94.8% | 95.2% |
| | Pre-meal | 97.1% | 97.2% | 97.6% |

Table 4a indicates that for the 30-g CHO meals, virtually no difference (in terms of the frequency of CGM values in the 70-180 mg/dL range) is realized by varying either the aggressiveness factor or the bolus timing. Similarly, Table 4b indicates only modest differences in this value.

Table 5 quantifies the difference in insulin infusion across the spectrum of algorithm aggressiveness, relative to the corresponding basal rates. The values are average algorithm-determined insulin delivery rates, as a difference relative to the corresponding basal rates (for example, a value of 0% implies that the algorithm delivered exactly the basal amount). The zone was defined throughout the simulations as 90-140 mg/dl. An entry of "n/a" indicates that there were no below-zone excursions for any of the 100 patients for that combination of aggressiveness factor and simulated protocol. All applicable values are negative (an entry of "n/a" implies that there were no below-zone excursions for any subject), indicating that even for the above-zone excursions, the algorithm was delivering less insulin than the corresponding basal rates. This counterintuitive result is likely due to the fact that most, if not all, above-zone excursions occurred in the wake of a meal and its corresponding bolus; the algorithm takes into account this bolus and therefore may limit its insulin infusion in the post-prandial times.

TABLE 5

Algorithm-determined insulin delivery during out-of-zone glucose excursions, as a function of the aggressiveness factor.

| Simulated protocol | Below-zone Excursions | | | Above-zone Excursions | | |
|---|---|---|---|---|---|---|
| | Conservative | Medium | Aggressive | Conservative | Medium | Aggressive |
| Mealtime boluses 30-g CHO meals | n/a | n/a | −83.1% | −6.4% | −6.1% | −4.1% |
| Pre-meal boluses 30-g CHO meals | n/a | n/a | n/a | −3.2% | −3.0% | −0.3% |
| Mealtime boluses 70-g CHO meals | −82.8% | −81.2% | −84.9% | −15.2% | −15.1% | −11.6% |
| Pre-meal boluses 70-g CHO meals | −82.2% | −80.9% | −83.2% | −8.6% | −7.3% | −2.1% |

The fundamental observation from Table 5 is that, as expected, greater aggressiveness results in more insulin delivered during above-zone excursions, but less insulin delivered during below-zone excursions.

Although the differences in both glucose concentration metrics and insulin infusion characteristics were subtle as the aggressiveness factor R varied from "conservative" to "aggressive," it is important to emphasize that this study was a simulation study. As such, it is possible that the effect of varying the aggressiveness factor is much more pronounced in actual human subjects.

While the invention has been described in terms of particular variations and illustrative figures, those of ordinary skill in the art will recognize that the invention is not limited to the variations or figures described. For example, the closed-loop controller need not be an MPC controller but can be, with appropriate modifications by those skilled in the art, a PID controller, a PID controller with internal model control (IMC), a model-algorithmic-control (MAC) that are discussed by Percival et al., in *"Closed-Loop Control and Advisory Mode Evaluation of an Artificial Pancreatic β Cell: Use of Proportional-Integral-Derivative Equivalent Model-Based Controllers"* Journal of Diabetes Science and Technology, Vol. 2, Issue 4, July 2008. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A method to control an infusion pump with a controller to control the pump and receive data from at least one glucose sensor, the method comprising:
   measuring glucose level in the subject with the glucose sensor to provide at least one glucose measurement in each time interval in a series of discrete time interval index ("k");
   obtaining in the controller a glucose calibration measurement of the glucose sensor during at least one time interval in the series of time interval index to provide for a calibration index;
   ascertaining whether one or more glucose measurements were not provided by the glucose sensor during a time interval of the series of time interval index to provide for an omission index;
   determining a tuning factor based on both the calibration index and omission index;
   calculating insulin amount for delivery by the controller based on a model predictive controller that utilizes (a) the plurality of glucose measurements to predict a trend of the glucose level from estimates of a metabolic state of the subject and (b) the tuning factor so as to provide a calculated insulin amount to be delivered to the subject for each interval of the interval index;
   delivering insulin amount determined from the calculating step with the infusion pump.

2. The method of claim 1, in which the tuning factor comprises an equation of the form $$R(k) = R_{NOM} + r_1 * CAL(k) + r_2 * MISSED(k)$$

where:
   R(k) comprises a tuning factor at each time interval index k such that $R_{MIN} \leq R(k) \leq R_{MAX}$;
   $R_{NOM}$ comprises a predetermined nominal tuning factor;
   k comprises a discrete time interval index;
   $R_{NOM} \leq R_{MAX} \leq 100 * R_{NOM}$;
   $R_{NOM}/100 \leq R_{MIN} \leq R_{NOM}$;
   $(R_{MAX} - R_{MIN})/500 \leq r_1 \leq (R_{MAX} - R_{MIN})/50$;
   $(R_{MAX} - R_{MIN})/50 \leq r_2 \leq (R_{MAX} - R_{MIN})/5$;
   CAL(k) comprises a calibration index in which
   $CAL(k) = k - k_{cal} - 6$ (for $k - k_{cal} \geq 6$) or
   $CAL(k) = k - k_{cal2} - 6$ (for $k - k_{cal} < 6$);
   $k_{cal}$ comprises the sample index of the most recent calibration for the continuous glucose sensor;
   $k_{cal2}$ comprises the sample index of the second most recent calibration for the continuous glucose sensor;
   MISSED(k) comprises an omission index in which one or more glucose values during the series of time intervals of the index k are missing or unreported to the controller.

3. The method of claim 2, in which the at least one glucose sensor comprises a continuous glucose sensor and an episodic glucose meter.

4. The method of claim 2, in which $r_1$ comprises any number from about 1 to about 50 and for $r_2$ comprises any number from about 10 to about 500.

5. A system for management of diabetes comprising:
   an episodic glucose meter to measure blood glucose of a subject at discrete non-uniform time intervals and provide such episodic blood glucose level as a calibration index for each interval in a time interval index (k);
   a continuous glucose monitor to continuously measure glucose level of the subject at discrete generally uniform time intervals and provide the glucose level at each interval in the form of glucose measurement data, in which any omission of a glucose measurement in any interval is stored in an omission index;

an insulin infusion pump to deliver insulin;

a controller in communication with the pump, glucose meter and the glucose monitor in which the controller determines a tuning factor based on (a) a calibration index derived from episodic blood glucose measurement and (b) an omission index for a model-predictive-control such that controller determines an insulin delivery rate for each time interval in the time interval index (k) from the model predictive control based on (1) desired glucose concentration, (2) glucose concentration measured by the monitor at each interval of the interval index (k), and (3) the tuning factor.

6. The system of claim 5, in which the tuning factor comprises an equation of the form $$R(k)=R_{NOM}+r_1*CAL(k)+r_2*MISSED(k)$$

where:

R(k) comprises a tuning factor at each time interval index k such that $R_{MIN} \leq R(k) \leq R_{MAX}$;

$R_{NOM}$ comprises a predetermined nominal tuning factor;

k comprises a discrete time interval index;

$R_{NOM} \leq R_{MAX} \leq 100*R_{NOM}$;

$R_{NOM}/100 \leq R_{MIN} \leq R_{NOM}$;

$(R_{MAX}-R_{MIN})/500 \leq r_1 \leq (R_{MAX}-R_{MIN})/50$;

$(R_{MAX}-R_{MIN})/50 \leq r_2 \leq (R_{MAX}-R_{MIN})/5$;

CAL(k) comprises a calibration index in which

CAL(k)=$k-k_{cal}-6$ (for $k-k_{cal} \geq 6$) or

CAL(k)=$k-k_{cal2}-6$ (for $k-k_{cal}<6$);

$k_{cal}$ comprises the sample index of the most recent calibration for the continuous glucose sensor;

$k_{cal2}$ comprises the sample index of the second most recent calibration for the continuous glucose sensor;

MISSED(k) comprises an omission index in which one or more glucose values during the series of time intervals of the index k are missing or unreported to the controller.

7. The system of claim 6, in which $r_1$ comprises any number from about 1 to about 50 and for $r_2$ comprises any number from about 10 to about 500.

* * * * *